United States Patent [19]

Weissman

[11] Patent Number: 5,120,223
[45] Date of Patent: Jun. 9, 1992

[54] APPARATUS AND METHOD FOR DENTAL PROSTHESIS

[76] Inventor: Bernard Weissman, 225 E. 48th St., New York, N.Y. 10017

[21] Appl. No.: 704,233

[22] Filed: May 22, 1991

Related U.S. Application Data

[60] Division of Ser. No. 446,756, Dec. 6, 1989, Pat. No. 5,037,300, which is a continuation of Ser. No. 193,328, May 12, 1988, Pat. No. 4,992,049.

[51] Int. Cl.$^5$ .............................................. A61C 5/00
[52] U.S. Cl. .................... 433/215; 433/220; 433/223; 433/225
[58] Field of Search .............. 433/165, 166, 167, 169, 433/173, 174, 215, 218, 220, 221, 223, 225

[56] References Cited

U.S. PATENT DOCUMENTS

| | | | |
|---|---|---|---|
| 2,250,058 | 7/1941 | Brooks | 433/166 |
| 2,366,767 | 1/1945 | Brooks | 433/166 |
| 2,438,725 | 3/1948 | Tamarin | 433/225 |
| 2,453,696 | 11/1948 | Brooks | 433/165 |
| 2,562,587 | 7/1951 | Swearingen | 433/166 |
| 3,461,563 | 8/1969 | Nelson | 433/165 |
| 3,487,544 | 1/1970 | Weissman | 433/218 |
| 4,447,210 | 5/1984 | Hidaka et al. | 433/173 |
| 4,490,116 | 12/1984 | Deutsch et al. | 433/215 |
| 4,713,004 | 12/1987 | Linkow et al. | 433/174 |

*Primary Examiner*—John J. Wilson
*Attorney, Agent, or Firm*—Paul J. Sutton; Barry G. Magidoff

[57] ABSTRACT

A dental tool is disclosed having a hollow cylindrical body portion, with an enlarged angular ring at one end, said ring having an abrasive coating thereon. The size and configuration of the enlarged annular ring allows the tool to be used to undercut the tooth surfaces in various ways, thereby allowing new methods in the securing of dental prostheses to existing teeth or to the jaw itself, or to the augmentation, or grafting, of bone material to reinforce a tooth, including (a) the creation of an undercut groove at the base of a prepared tooth into which a gasket can be positioned to form a seal with the dental prosthesis (b) the drilling of an annular or cylindrical cavity with an undercut portion in a tooth or jaw bone into which a shaped insert can be securely mounted, which insert can act as a mounting for a dental prosthesis, and (c) harvesting a core or plug of bone material from a jaw bone, crushing the harvested bone and implanting said harvested bone around a tooth situated in the same jaw as the crushed bone was harvested, as a bone augmentation procedure to strengthen said tooth.

24 Claims, 16 Drawing Sheets

FIG. 20
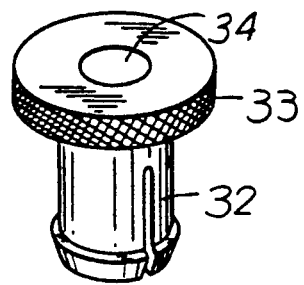
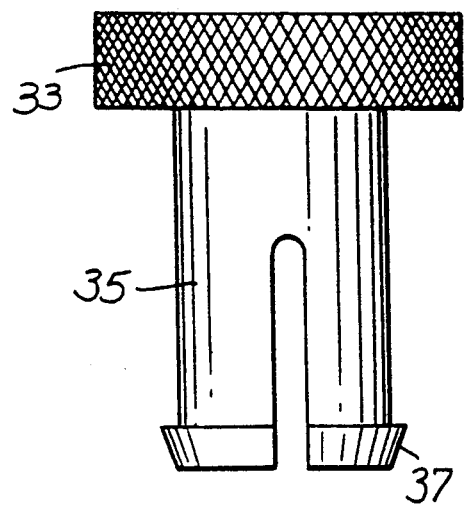
FIG. 22
FIG. 21
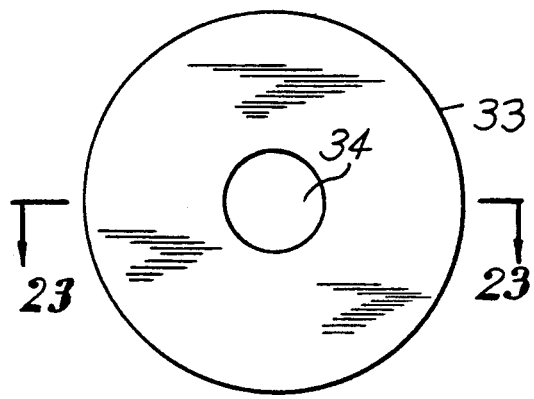
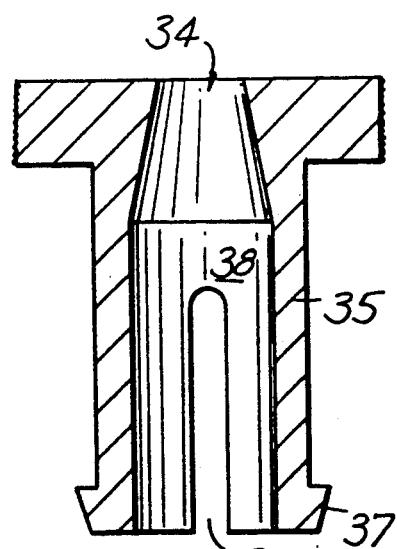
FIG. 23

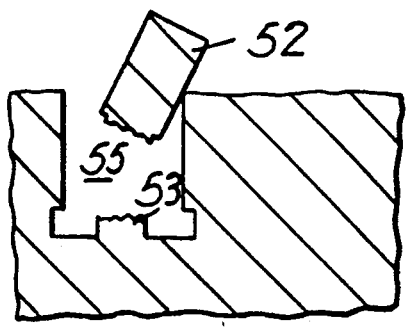
FIG. 40
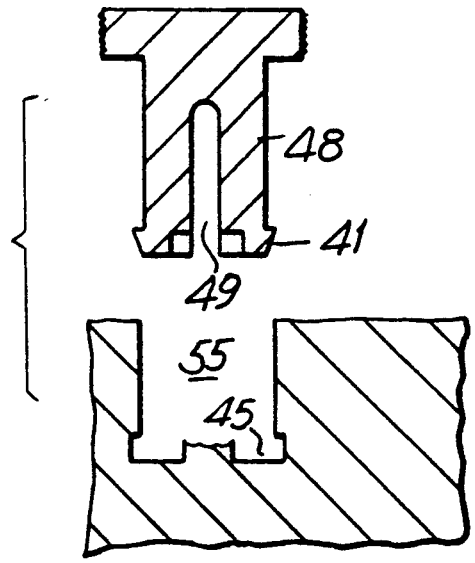
FIG. 41
FIG. 42
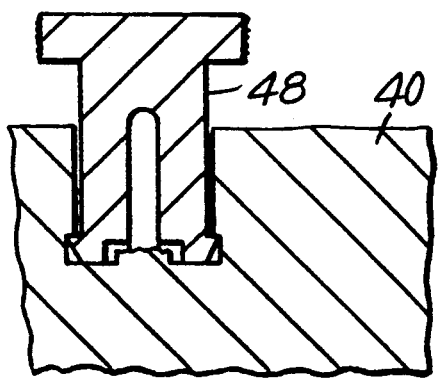

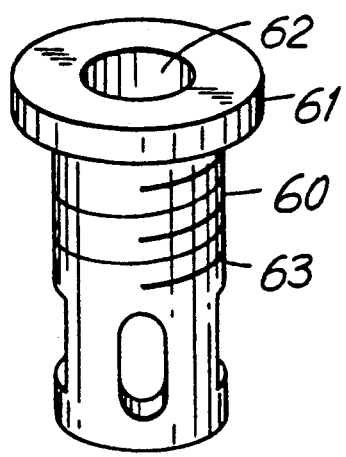
FIG.43
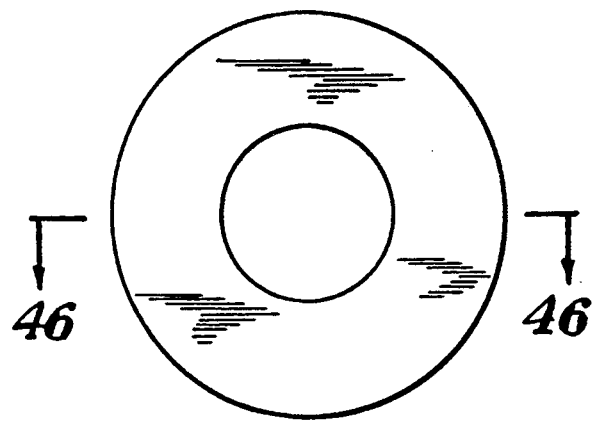
FIG.44
FIG.45
FIG.46
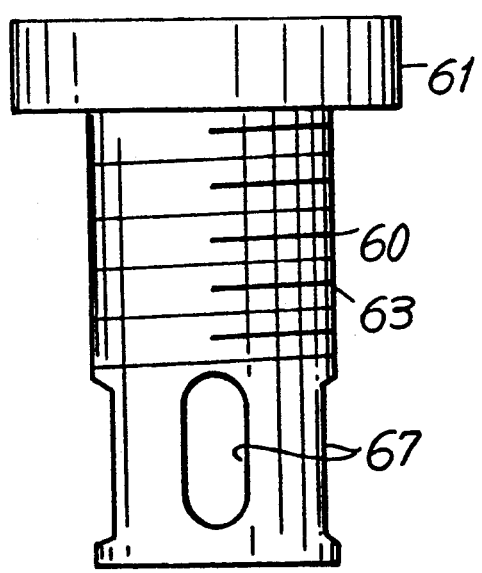
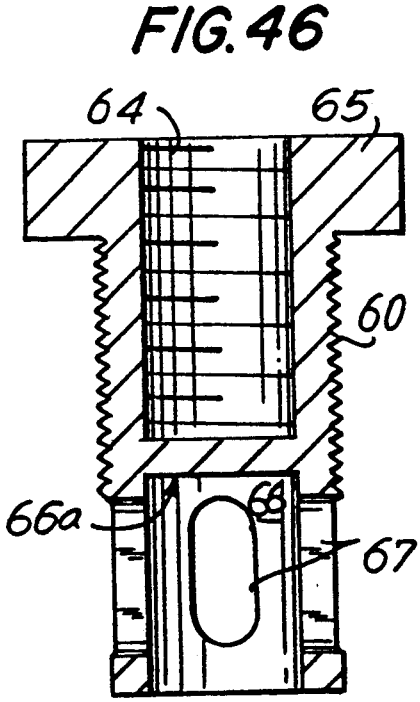

APPARATUS AND METHOD FOR DENTAL PROSTHESIS

CROSS REFERENCE TO RELATED APPLICATIONS

This is a division of application Ser. No. 07/446,756 filed Dec. 6, 1989, now U.S. Pat. No. 5,037,300, which is a continuation in part of Application Ser. No. 07/193,328 filed May 12, 1988 now U.S. Pat. No. 4,992,049.

BACKGROUND OF THE INVENTION

1. Field of the Invention

The present invention relates to a tool to be used in dentistry and the use of this tool in new methods for the enplacement of dental prostheses. More particularly, the present invention relates to a tool which allows excavation or undercutting of a tooth or jaw bone in different configurations and depths, which may be used to (a) form an indentation around the base of a prepared tooth into which a gasket can be inserted to seal a veneer, crown or jacket in place on the tooth, (b) form either an annular or cylindrical hole in a tooth or jaw to receive an insert upon which a crown or artificial tooth can be mounted, or (c) obtain a plug of bone material, which harvested bone material can be crushed to granular particles and placed around the base of a tooth as a bone augmentation and strengthening procedure.

2. State of the Art

It is conventional practice in dentistry to apply a veneer prosthesis to a tooth which has been damaged either as a result of trauma or disease, i.e. caries. Generally, the surface enamel of the tooth is partially removed by grinding to form a relatively even surface, a mold is taken of the tooth and the surrounding portion of the mouth to form a prosthesis, which is then adhesively secured to the previously ground down surface.

Such a veneer is generally not subject to the extreme structural stress to which the facing transverse surfaces of teeth are subject, but rather, is applied to a vertical, buccal or labial surface. The veneer is intended primarily for cosmetic purposes, but also to protect the remaining enamel of the tooth from further damage caused by chemical or bacterial action. Great care must be taken to insure that the veneer is securely applied to the tooth substrata so as to not only be cosmetically satisfactory, but also insure against stress during chewing. Dentists must carefully place the veneer against the surface, and by eye insure that it has been properly placed.

In teeth which have received more extensive damage, major portions of the tooth's surface may be replaced by a crown. Normally the surface is prepared to a desired shape which will help retain the crown. A mold is then made of the remaining prepared tooth in order to shape the portion of the crown which will be in contact with the tooth. The resulting crown is thereafter mounted on the prepared tooth. Various tools have been developed to shape the tooth, such as seen in U.S. Pat. No. 2,250,058 issued Apr. 8, 1940 to Brooks, or U.S. Pat. No. 4,473,354 issued Sep. 25, 1984 to Rigaud. Additionally, a post may be mounted in the tooth or in the underlaying jaw as an aid to holding a crown or artificial tooth in place.

SUMMARY OF THE INVENTION

It is an object of the present invention to provide a new tool which will allow the dentist to use improved procedures for the attachment of veneers, jackets or crowns to teeth, or the implanting of artificial teeth or crowns directly into the jaw. This tool and related procedures will improve the efficiency of prior art procedures to accomplish similar purposes, and to strengthen the bonding and stability of such veneers, jackets, crowns and artificial teeth (hereinafter collectively referred to as "dental prosthesis") mounted by use of such tool and procedures. It is yet a further object of the present invention to provide a new, improved tool for more efficiently preparing the tooth or jaw for applications of a dental prosthesis, and for so securing the dental prosthesis to its supporting substrata. Yet a further object of the invention is to provide a tool and procedure for augmenting bone around a weakened natural tooth where the surrounding bone has withered by obtaining and crushing a plug of bone material and implanting said crushed bone around said tooth.

These and other objects are achieved in accordance with the present invention through the employment of the tool of the present invention. The tool has an elongated shank portion, one end of the shank portion being designed to be conventionally secured to a driving member, such as a dentist's drill handpiece, for causing rotation of the tool. The remainder of the tool is in the form of a hollow shaft. At the end of the shaft farthest from the shank, there is an enlarged annular ring having a larger outer diameter and a smaller inner diameter than the hollow portion of the shaft.

A cutting surface, such as an abrasive coating, is secured to at least the outermost circumferential surface of said enlarged annular ring. When the tool is to be used to make an annular or cylindrical hole in a tooth or jaw or to obtain a cylindrical plug of bone, the bottom of the enlarged annular ring (i.e. the transverse surface farthest from the shank) and the innermost circumferential surface must also be coated with abrasive material. When so used, the hollow shaft can have a device to limit the depth of penetration of the tool into the tooth or bone, such as a depth limiting surface mounted in the hollow shaft with a means for accurately varying the perpendicular distance between the depth limiting surface and the bottom surface of the enlarged annular ring.

Since the tool is designed to work in or on a tooth, the outer diameter of the annular ring should be substantially less than that of a tooth and would normally be on the order of 3 mm to 4 mm. The enlarged outer diameter of the annular ring in comparison with that of the hollow shaft limits engagement of the tool with the tooth to the surface of the annular ring, thereby reducing the heat generated through friction. The tool may be hollow throughout to allow liquid or air cooling of the drilling operation and for chip and ground tooth displacement and removal during drilling. As a further aid in removal of ground material, the hollow shaft may have one or more openings which allow communication and passage of material between the interior of the hollow shaft and the space between the outer diameter of the hollow shaft and the wall of the hole in the tooth or jaw formed by the cutting surfaces of the tool.

The size and configuration of the enlarged annular ring allows the tool to be used to undercut the tooth surfaces in various ways, thereby allowing new methods in the securing of dental prostheses to existing teeth or to the jaw itself, or to the augmentation, or grafting, of bone material to reinforce a tooth, including (a) the creation of an undercut groove at the base of a prepared tooth into which a gasket can be positioned to form a seal with the dental prosthesis; (b) the drilling of an annular or cylindrical cavity with an undercut portion in a tooth or jaw bone into which a shaped insert can be securely mounted, which insert can act as a mounting for a dental prosthesis; and (c) harvesting a core or plug of bone material from a jaw bone, crushing the harvested bone and implanting said harvested bone around a tooth situated in the same jaw as the crushed bone was harvested, as a bone augmentation procedure to strengthen the support for said tooth.

BRIEF DESCRIPTION OF THE DRAWINGS

Further details of the present invention are shown in the accompanying drawing, by way of example and not by way of exclusion Many portions of the invention, or the context thereof, are shown in schematic representation, where greater detail is unnecessary as it is apparent or well known to those skilled in the art. Referring to the accompanying drawings

FIG. 20 is a perspective view of an insert for mounting in an annular hole made in a tooth by the tool of FIG. 1;

FIG. 21 is a top view of the insert of FIG. 20;

FIG. 22 is a side view of the insert of FIG. 20;

FIG. 23 is a cross sectional view of the insert of FIG. 20 taken along Plane 23—23 of FIG. 21;

FIG. 36 through FIG. 42 are diagrammatical cross sectional representations of the use of the tool of FIG. 1 to excavate a substantially cylindrical hole in a tooth with an enlarged undercut portion in which the insert of FIG. 32 is mounted;

FIG. 43 is a perspective view of an insert for mounting in a hole made in a jaw bone by the tool of FIG. 1;

FIG. 44 is a top view of the insert of FIG. 43;

FIG. 45 is a side view of the insert of FIG. 43;

FIG. 46 is a cross sectional view of the insert of FIG. 43 taken along Plane 46—46 of FIG. 44;

DETAILED DESCRIPTION OF THE ILLUSTRATED EMBODIMENTS

Figure 1:
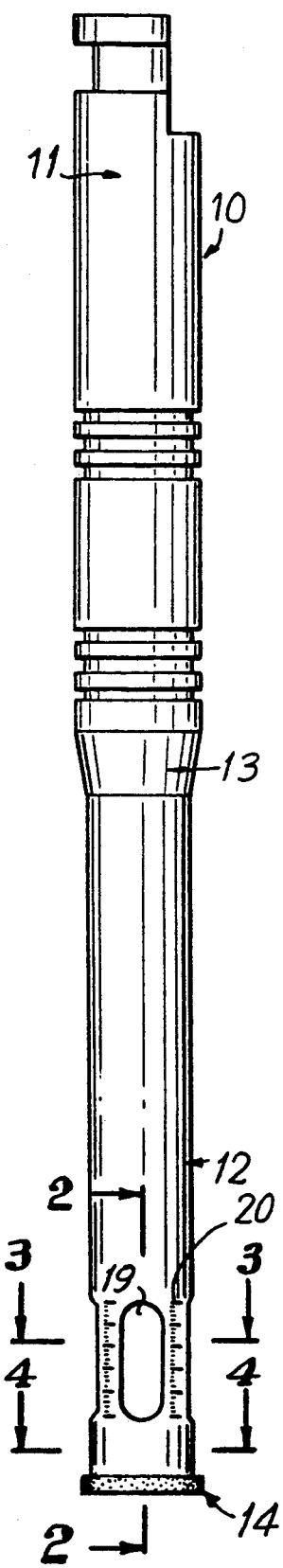
FIG. 1 is a side view of a tool in accordance with the present invention.

FIGS. 1-6 show the dental tool 10 of the present invention. The tool 10 has an elongated shank portion 11 of conventional construction to be secured to a rotational driving means, such as a latch or friction grip type handpiece on a dentist's drill The remainder of the tool 10 primarily consists of a shaft 12 of smaller diameter than shank 11. The shank 11 and the shaft 12 are connected by a beveled section 13.

The portion of the shaft 12 farthest from the shank 11 has a cavity 18 therein. At the end of the shaft 12 farthest from the shank 11, there is an enlarged annular ring 14 which define the opening into cavity 18. The outer diameter of the annular ring 14 has a larger diameter than the outer diameter of shaft 12. Equally, the inner diameter of the annular ring 14 is less than the inner diameter of the hollow portion of the shaft 12.

Since the tool is designed to work in or on a tooth, the outer diameter of the annular ring 14 is substantially less than that of a tooth. Typically, the diameter of the shaft 12 is on the order of 3.5 mm and the difference between the outer diameter of the annular member and its inner diameter is 1.2 mm.

The cutting surface of the tool 10 is in the form of an abrasive coating secured to the outer circumferential surface 15, the inner circumferential surface 16, and the bottom 17 of annular ring 14. It may be formed by any conventional abrasive coating for dental drill bits and the like.

The radial distance between the outer diameter of the annular member 14 and the outer diameter of the shaft 12 is greater than the radial distance between the inner diameter of the hollow portion of shaft 12 and the inner diameter of the annular member 14. Among other things, this assures that when the tool 10 is used to an undercut an annular or cylindrical hole in the surface of a tooth or jaw, a space will remain between the outer surface of the hollow shaft 12 above the enlarged annular member 14 and the excavated wall of the tooth or jaw, as will be more fully discussed below. The clearance between the outer surface of the annular ring 14 to the outer surface immediate adjacent portion of shaft 12 acts to limit the heat generated from frictional engagement of the tool 10 with a tooth or jaw bone to the immediate area of the annular ring 14. The enlarged size of the annular ring 14 also aids in dissipating any such heat generated. While the annular member 14 and, in particular, its outer wall 15 have been shown as cylindrical, the annular ring may take other forms, such as having a beveled, stepped, or curved outer surface 15.

Figure 2:
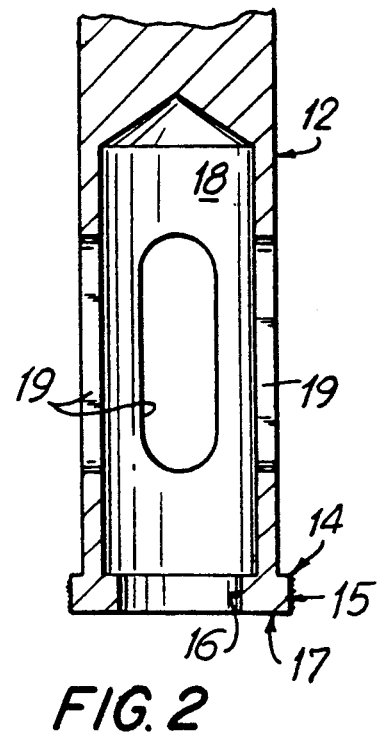
FIG. 2 is an enlarged fragmentary cross sectional view of the lower portion of the tool of FIG. 1 taken along Plane 2—2.

As seen in FIG. 2, the hollow portion 18 of shaft 12 does not extend the entire length of the shaft 12. The tool 10, however, may have a hollow passage throughout to allow passage of a stream of liquid or air for cooling of the drilling operation and/or for bone chip and ground tooth displacement and removal.

Figure 3:
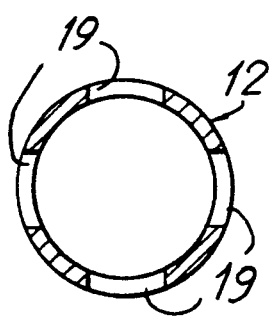
FIG. 3 is an enlarged cross sectional view of the lower portion of the tool of FIG. 1 taken along Plane 3—3.
Figure 4:
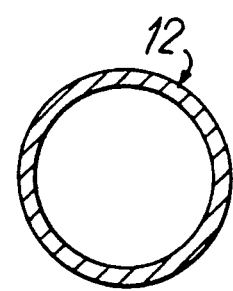
FIG. 4 is an enlarged cross sectional view of the lower portion of the tool of FIG. 1 taken along Plane 4—4.
Figure 5:
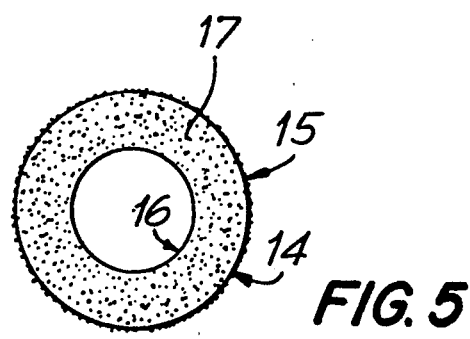
FIG. 5 is a bottom view of the tool of FIG. 1.
Figure 6:
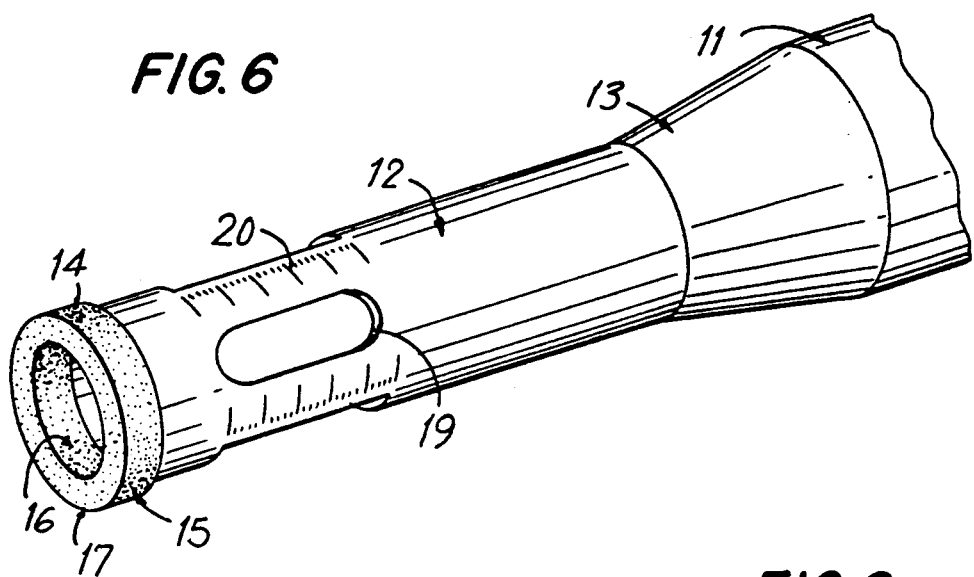
FIG. 6 is an enlarged perspective view of the lower portion of the tool of FIG. 1.

To allow the passage of ground tooth or bone away from the drilling surface, the hollow shaft 12 may have one or more openings 19 communicating with the interior hollow portion 18 of shaft 12. As seen in FIGS. 1 and 3, in the preferred embodiment, four such openings 19 are spaced equally around the circumference of the shaft 12. The openings 19 allow communication and passage of material between the interior cavity 18 of shaft 12 and the space between the outer diameter of the shaft 12 and the walls of the hole being excavated by the tool. The openings 19 also allow for insertion of a tool (not shown) for removal of any solid cylindrical material trapped in the hollow portion 18 of shaft 12.

The openings 19 may have calibrations 20 aligned therewith to allow a visual determination of the depth of a hole excavated by the tool 10. Alternatively, to control the depth of excavation, a plug having a screw thread which would co-act with a thread in cavity 18 or other limiting device (not shown) may be positioned in cavity 18. The calibrations 20 may be used in conjunction with openings 19 to position the plug or other limiting device within cavity 18, providing a depth limiting surface which would prevent further drilling of the tooth. Openings 19 could also aid in the removal of the plug o other limiting device.

The size and configuration of the enlarged annular ring 14 allows the drill to be used to undercut a tooth's surface in various ways. For example, the tool 10 can be used to form the undercut groove 26 in a tooth 24 prepared to receive a dental prosthesis 28. A gasket 29 can be mounted in the undercut groove 24 to form a seal between the dental prosthesis 28 and the prepared tooth 24.

Figure 7:
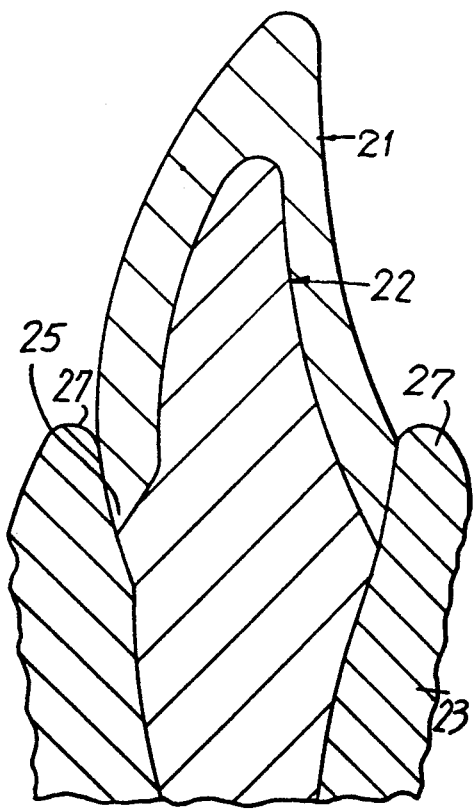
FIG. 7 is a cross sectional schematic representation of a side of a tooth showing both the original dentine and the shape of a core of the tooth, when prepared to receive a dental prosthesis.
Figure 8:
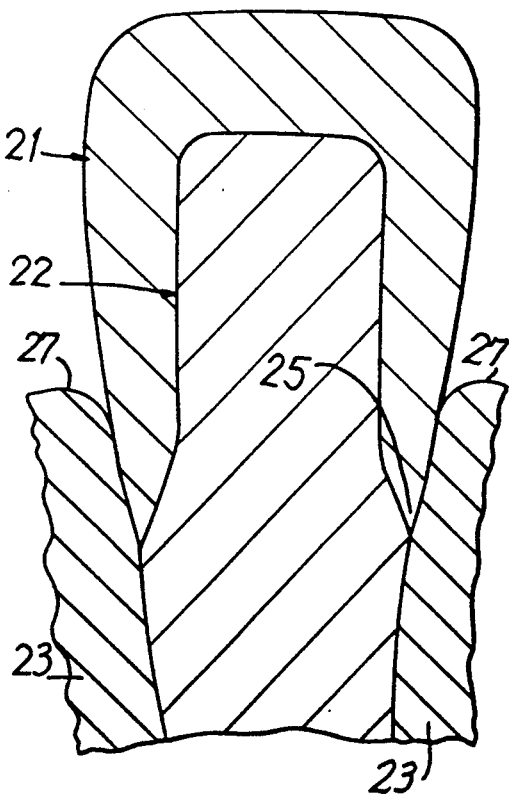
FIG. 8 is a cross sectional schematic representation of the front of the tooth of FIG. 7 showing both the original dentine and the shape of a core of the tooth, as prepared to receive a dental prosthesis.

As seen in FIGS. 7 and 8, to prepare a tooth to receive a dental prosthesis, at least a portion of the enamel 21 is removed in any conventional manner to form a prepared core 22. This results in the prepared core 22 having a shoulder 25 adjacent the gum 23 at or slightly below the gum line 27.

Figure 9:
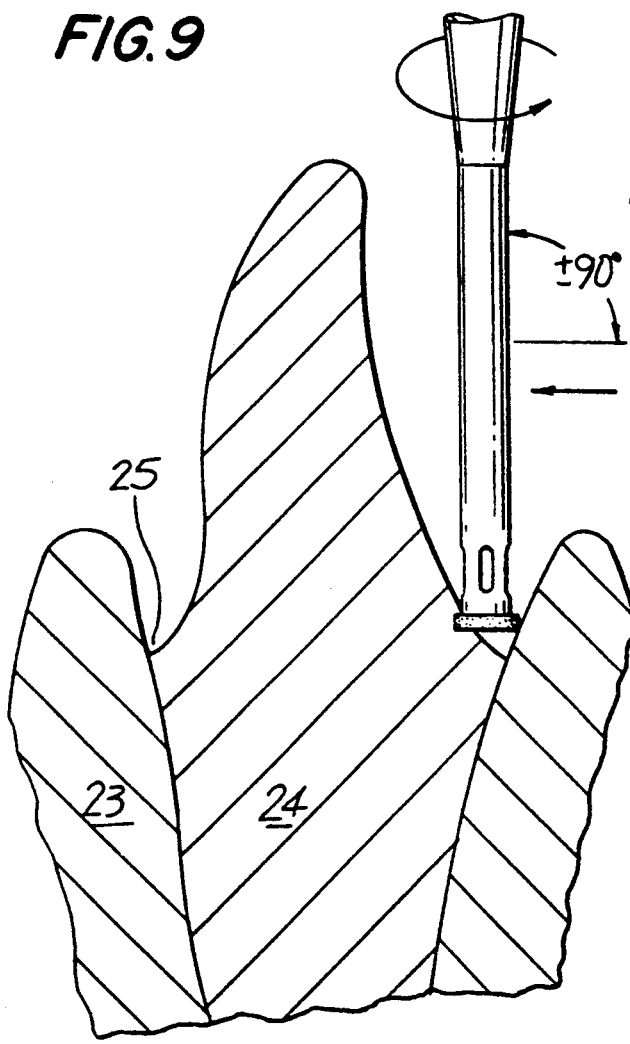
FIG. 9 is a pictorial representation (partly shown in cross section) of the tool of FIG. 1 being used to place a groove around the base of a prepared core of a tooth (shown in cross section), thereby creating an undercut in the prepared tooth core
Figure 10:
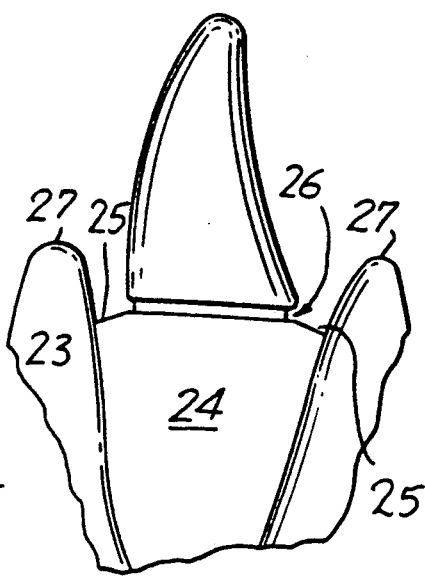
FIG. 10 is a side view of a prepared tooth having an undercut in accordance with the present invention.
Figure 11:
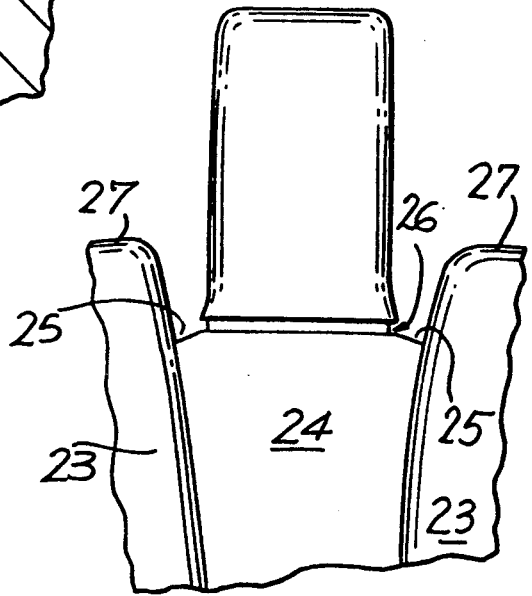
FIG. 11 is a front view of a prepared tooth having an undercut in accordance with the present invention.
Figure 12:
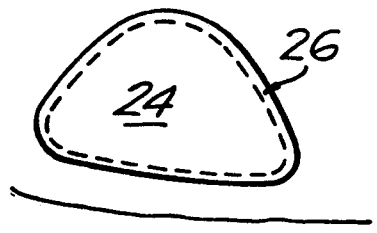
FIG. 12 is a top view of a tooth having an undercut in accordance with the present invention where the undercut portion is shown by a dotted line.
Figure 13:
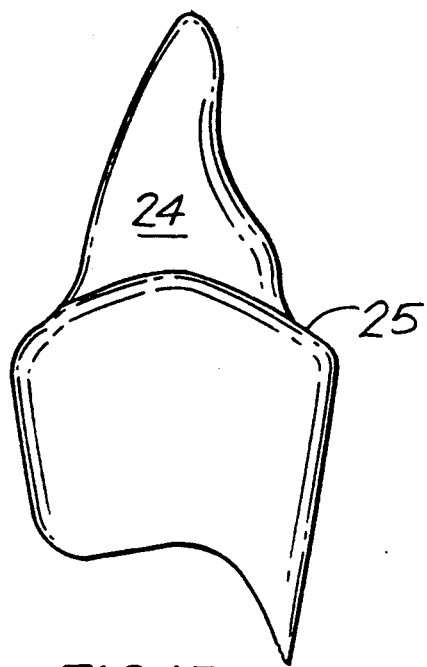
FIG. 13 through FIG. 16 are schematic representations in chronological order, depicting the use of the tool of FIG. 1 on an already prepared tooth to further shape the tooth, as well as undercut the prepared core, and the use of such an undercut to securely hold a dental prosthesis (shown in cross section) in place.
Figure 14:
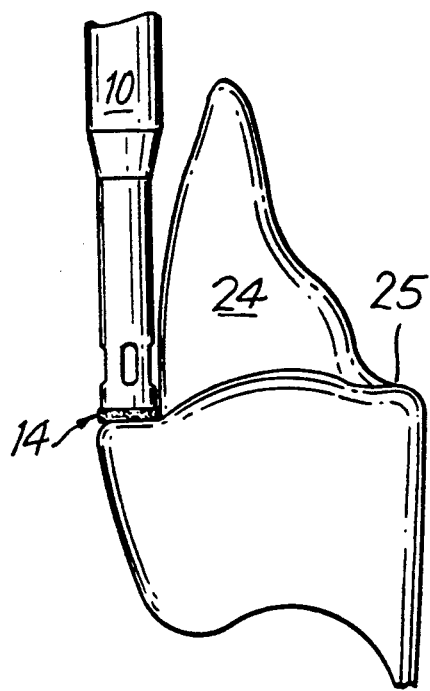
Figure 15:
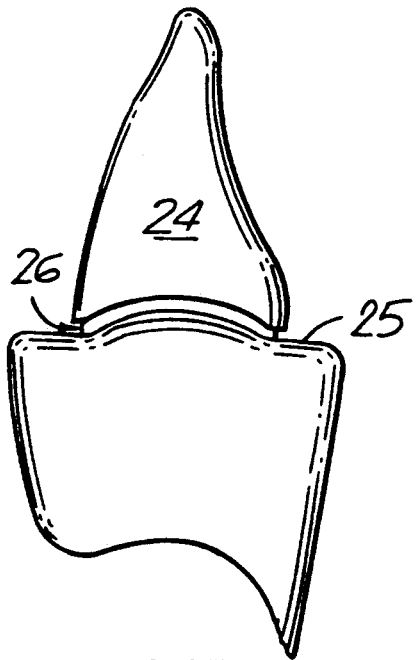
Figure 16:
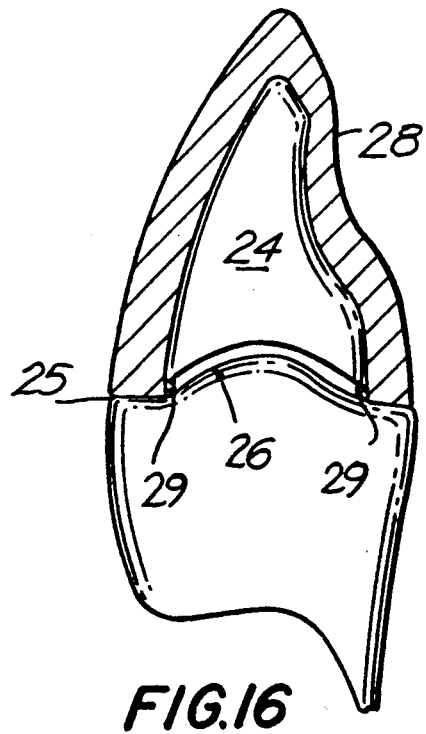

As shown in FIG. 9, the tool 10 of the present invention is used in connection with an already prepared tooth 24 which has had the outer enamel removed. The tool 10 is rotated by a dentist drill (not shown). It is moved around the shoulder 25 of prepared tooth 24 while being pressed against the shoulder 25 of the prepared tooth 24. The outer circumferential surface 15 of the enlarged annular ring 14 acts to form an undercut indentation or channel 26 around the entire circumference of the tooth 24 at or underneath the gumline 27. Since the abrading action is radial rather than axial, if the instrument 10 is to be used only for this purpose, it is unnecessary for abrasive coating to be placed on the bottom surface 17 of the tool 10.

The tool 10, however, may be used to not only form channel 26 in the prepared tooth 24, but to further shape the shoulder 25 of the tooth 24 by means of the abrasive bottom surface 17. As seen in FIGS. 13 through 16, simultaneously with the formation of the undercut 26, the shoulder 25 of the already prepared tooth 24 can be further shaped, i.e. flattened and otherwise worked, by the abrasive bottom surface 17 of the annular member 14, to better prepare the tooth 44 to receive a dental prosthesis 28.

Figure 17:
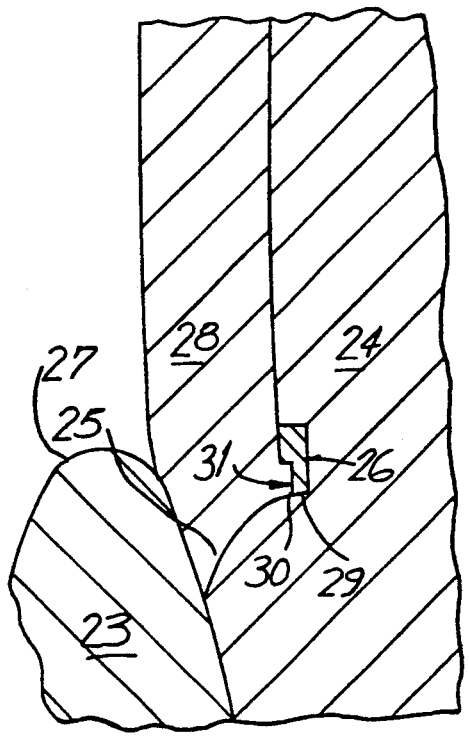
FIG. 17 is an enlarged view of the undercut portion of a tooth as shown in FIG. 16 having a gasket positioned in the undercut portion of the tooth to seal the dental prosthesis to the tooth.
Figure 18:
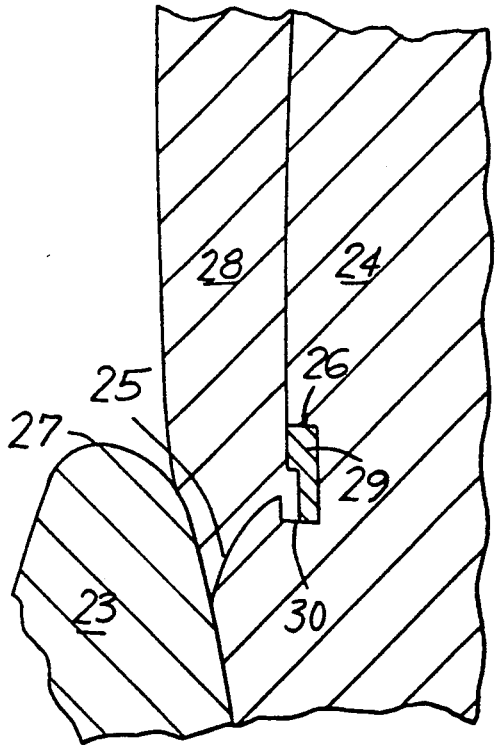
FIG. 18 is an enlarged view of the undercut portion of the tooth of FIG. 16, showing an alternative shape of undercut in which the undercutting extends further axially into the tooth.
Figure 19:
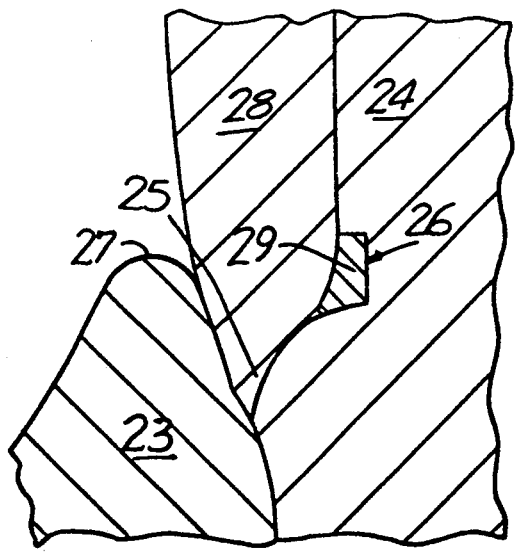
FIG. 19 is an enlarged view of the undercut portion of the tooth of FIG. 16 with a dental prosthesis mounted thereon, where the gasket completely fills the undercut portion.

As is seen in FIGS. 17 through 19, the channel 26 is used to further lock dental prosthesis 28 against the tooth core 24 and to form a seal between the dental prosthesis 28 and the core 24. As noted above, the prepared tooth 24 is undercut to form channel 26 around the base 25 of the tooth at or below the gum line 27. A gasket 29 shaped to tightly fit the channel 26 is set in channel 26. The gasket 29 may be made from any conventional dental gasket material. In order to insure the positive interlocking of the dental prosthesis 28 with the prepared core 24, the gasket may itself be undercut at 30. The dental prosthesis 28 would have a corresponding projection 31 to interlock with the cutaway portion 30 of gasket 29. Alternatively, a projection on the dental prosthesis 28 may directly mate and interlock with channel 26 (not shown).

As seen in FIG. 18, if a more positive interlock is desired between the dental prosthesis 28 and the core 24, after the tool 10 has been used to form a channel 26 as seen in FIG. 17, the tool 10 may be turned so that surface 15 is positioned against shoulder 25 at right angle to its former position in forming groove 26. The tool 10 is then moved radially toward the tooth root and around the tooth core 24 to extend groove 26 further into the tooth core 24. The undercut portion 30 of gasket 29 and the extended portion 31 are correspondingly shaped to fit together and to fit the extended groove 26. This forms an even more positive interlock between the dental prosthesis 28 and the prepared tooth core 24.

As seen in FIG. 19, a gasket 29 without an undercut can be mounted in the groove 26 in tooth 24. The gasket is shaped to completely fill the channel 26, and mate with the corresponding portion of dental prosthesis 28, sealing the interface between the dental prosthesis 28 and tooth core 24.

Tool 10 may also be used to drill an annular hole in the surface of the tooth for positively holding an insert 32 in position in the tooth. Such insert 32 can act as a post for holding a dental prosthesis (not shown) in position on a tooth. As seen in FIGS. 20 through 23, the insert 23 is generally cylindrical in shape with a cylindrical body portion 35 having an extended cavity 38 therein. Body 35 has a cylindrical top 33, which is enlarged in comparison with body 35, having a larger diameter. The top 33 has an opening 34 along its central axis. The opening 34 communicates with cavity 38 in the body portion 35. As an aid to adhering the insert 32 to a dental prosthesis (not shown), the top 33 of the insert 32 is knurled. The hollow body 35 of the insert 32 has two slots 36 diametrically opposite each other. Slots 36 allow the bottom of the insert 32 to be pressed together to allow insertion in a confined space. At the bottom of the body 35 is a flange 37 for interaction with the an undercut portion 45 of the hole 44 in which the insert 33 is to be mounted. The insert may be made of any suitable plastic or metal.

Figure 24:
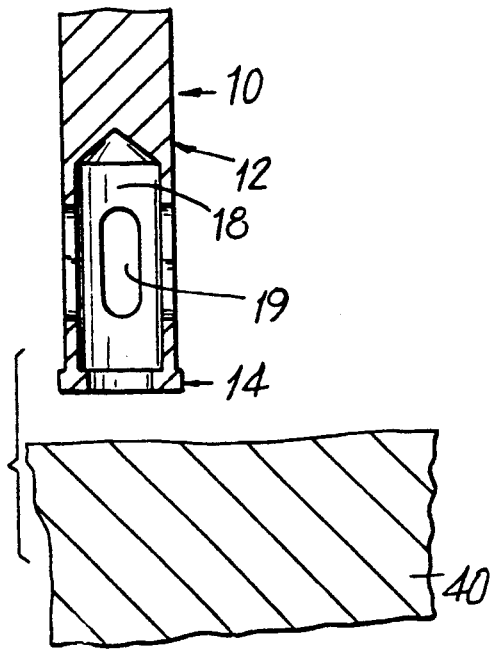
FIG. 24 through FIG. 31 are schematic cross sectional representations, in chronological order, depicting the use of the tool of FIG. 1 to excavate an annular passage in a tooth with an enlarged undercut portion into which the insert of FIG. 20 is secured.
Figure 25:
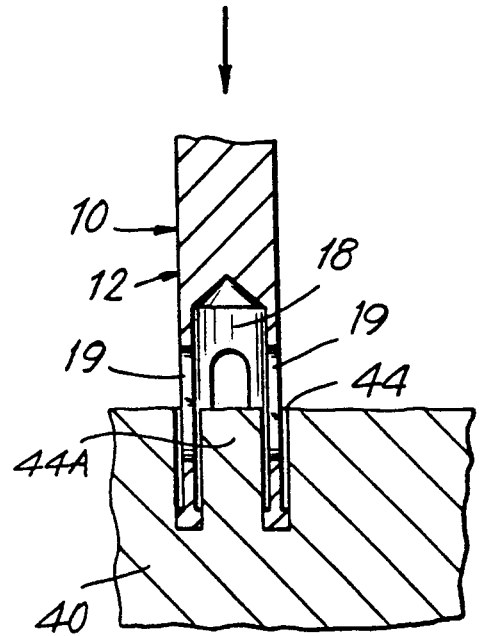
Figure 26:
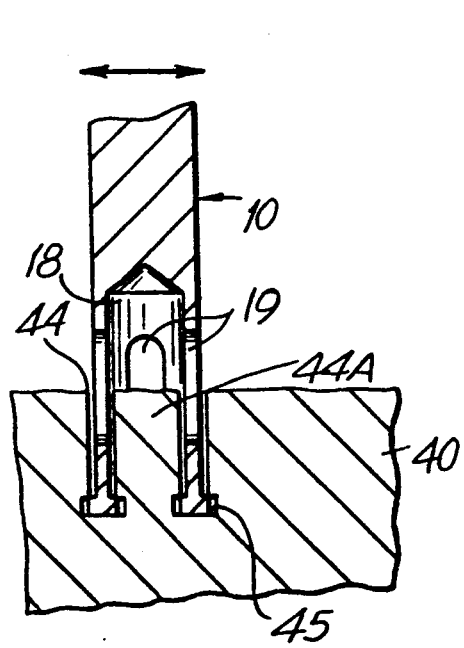
Figure 27:
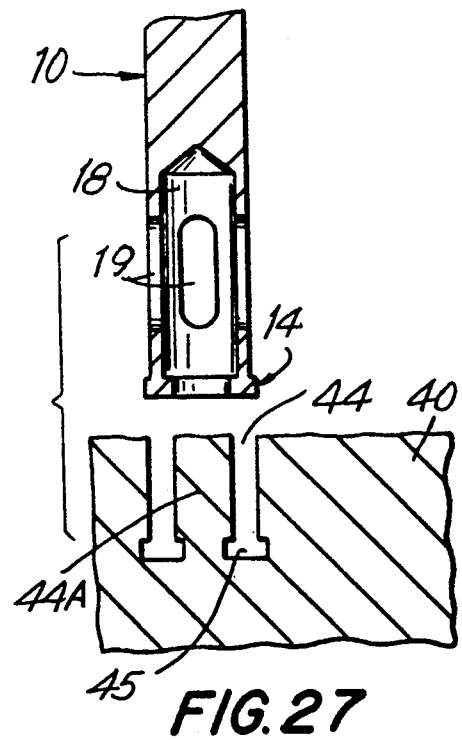
Figure 28:
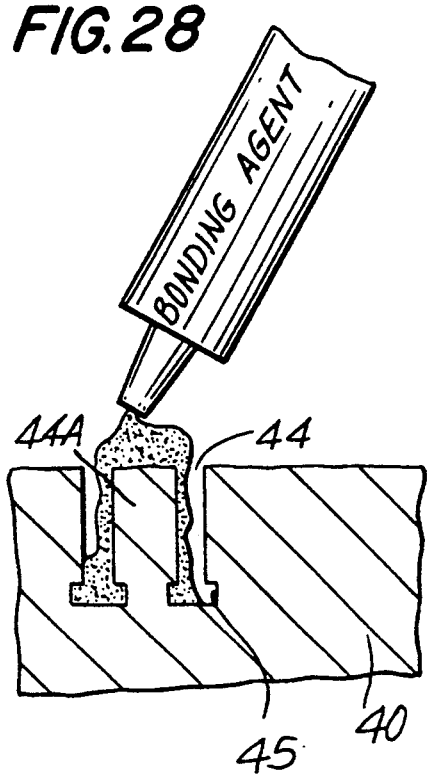
Figure 29:
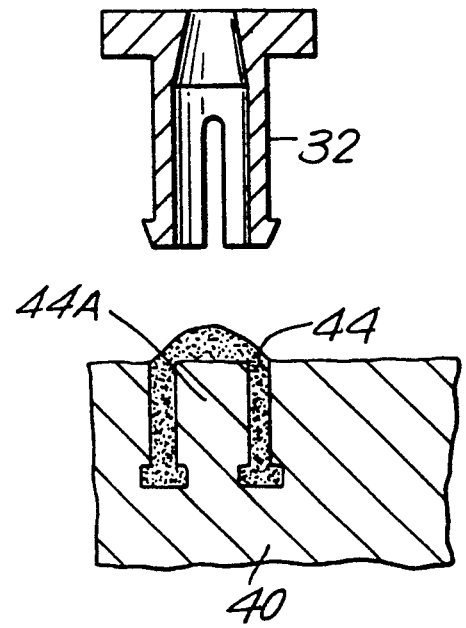

FIGS. 24 through 31 show the use of tool 10 in forming an annular hole 44 in a tooth 40 for holding insert 32 in place and the process for bonding insert 32 to the tooth 40. As seen in FIG. 24, tool 10 is positioned above the tooth 40 at the location in which the insert is to be mounted. The tool 10 is moved axially against the surface of the tooth 40, to drill an annular shaft or hole 44 into tooth 40. During this drilling operation, the removed tooth material can flow between of the hollow portion 18 of shaft 12 and the space 41 between the outer wall of the shaft 12 and the walls of the cavity 44 through openings 19 thereby facilitating the removal of such material for the drill site.

As previously discussed, the depth of drilling may be controlled visually through the markings 20 on the side of the tool 10, or through a use of a plug (not shown) or other depth limiting device positioned in hollow section 18 of shaft 12. After the desired depth is reached, the tool is moved radially to form an enlarged annular opening 45 at the bottom of the hole 44. The interior walls of the hollow portion 18 of shaft 12 and there interaction with the core 44a of the tooth material left after drilling of the annular hole 44 controls the size of annular opening 45. Since, as noted previously, the radial distance between the outer diameter of the annular member 14 and the outer diameter of the shaft 12 is greater than the radial distance between the inner diameter of the hollow portion of shaft 12 and the inner diameter of the annular member 14, the space 41 is always maintained between at least one surface of shaft 12 and the cavity wall 44 during the radial movement of tool 10 and the geometry of subsequent annular opening 45 is set.

After formulation of enlarged annular opening 45, the tool 10 is removed from hole 44. Hole 44 is then filled to overflowing with a conventional bonding agent.

Figure 30:
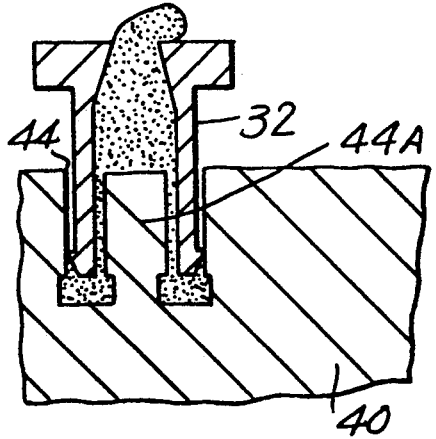
Figure 31:
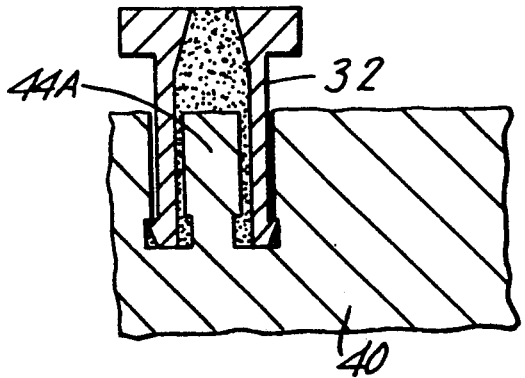
Figure 32:
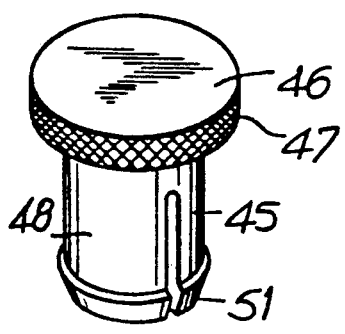
FIG. 32 is a perspective view of another embodiment of an insert for mounting in a substantially cylindrical hole made in a tooth by the tool of FIG. 1.
Figure 33:
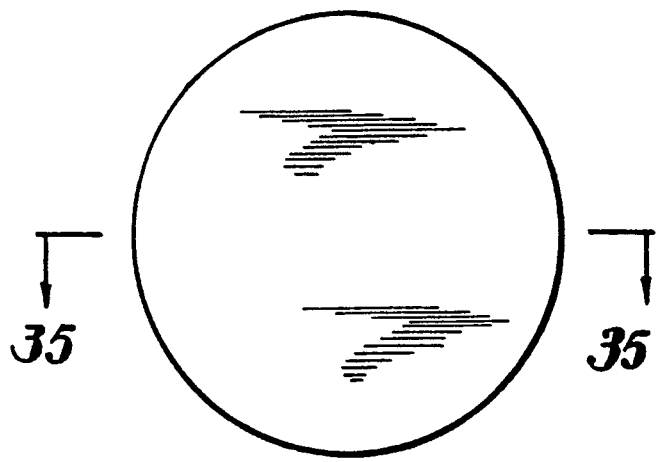
FIG. 33 is a top view of the insert of FIG. 32.
Figure 34:
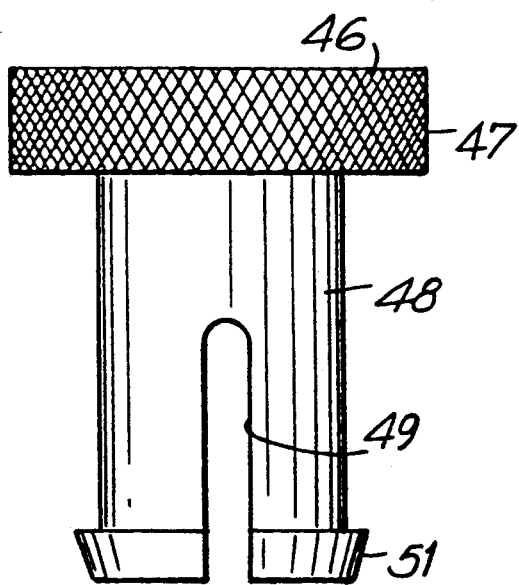
FIG. 34 is a side view of the insert of FIG. 32.
Figure 35:
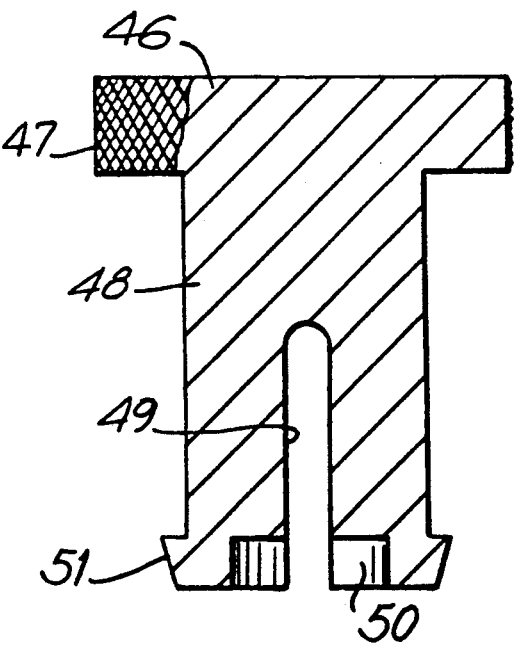
FIG. 35 is a cross sectional view of the insert of FIG. 32 taken along Plane 35—35 of FIG. 33.
Figure 36:
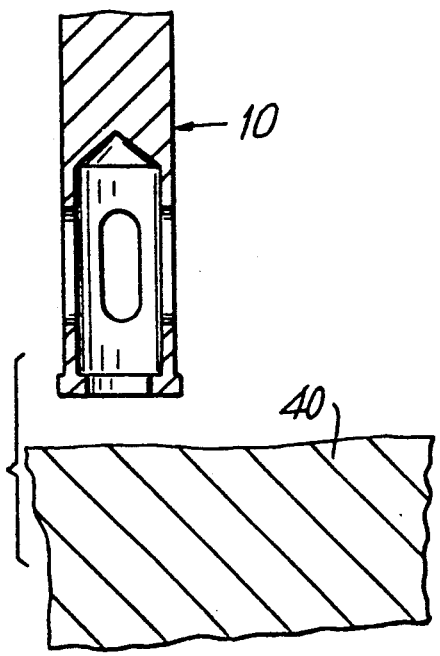
Figure 37:
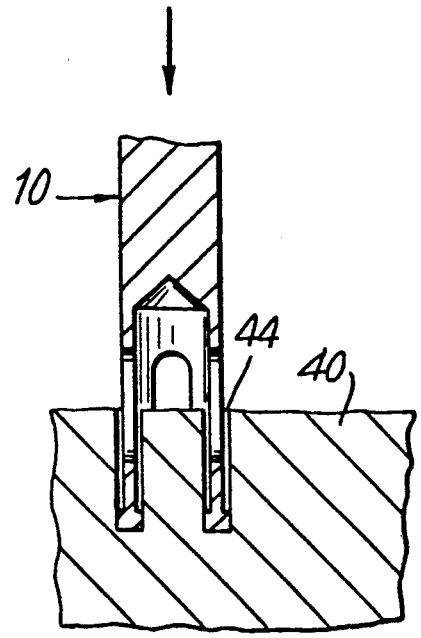

Central portion 35 of insert 32 approximately the dimension and shape of shaft 12. The outer diameter flange 37 is approximately the same as that of enlarged cavity 45. Accordingly, when as seen in FIG. 30 the insert 32 is forced into the filled hole 44, the sides of insert 32 will be forced to flex at slots 36 in order to enter hole 44. When fully inserted flange 37 will snap into enlarged opening 45 thereby positively interlocking the insert 32 with the tooth 40. The excess bonding agent passes through opening 34 in the top 33 of insert 32 which excess is then removed. After the bonding agent has fixed, the insert 32 may be used as a mounting post for a dental prosthesis (not shown).

Alternatively, tool 10 can be used to form an essentially cylindrical opening in a tooth 40. FIGS. 32 through 35 show as cylindrical insert 45 for use with such a cylindrical opening. It has a solid top 46, with a knurled outer surface 47 to aid bonding of the insert to a dental prosthesis (not shown). The main body of the insert 45 is a substantially solid cylindrical element 48 with a slot 49 therein to allow deflection of the insert 32 during insertion in a tooth. In addition, there is a small cylindrical cavity 50 at the bottom of the body 48. Flange 51 at the base of the body 48 is for interconnection with an enlarged opening 45 made by tool 10 in the base of the receiving hole 44.

Figure 38:
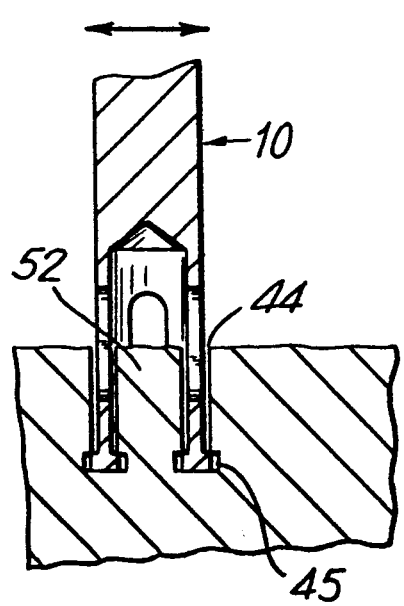
Figure 39:
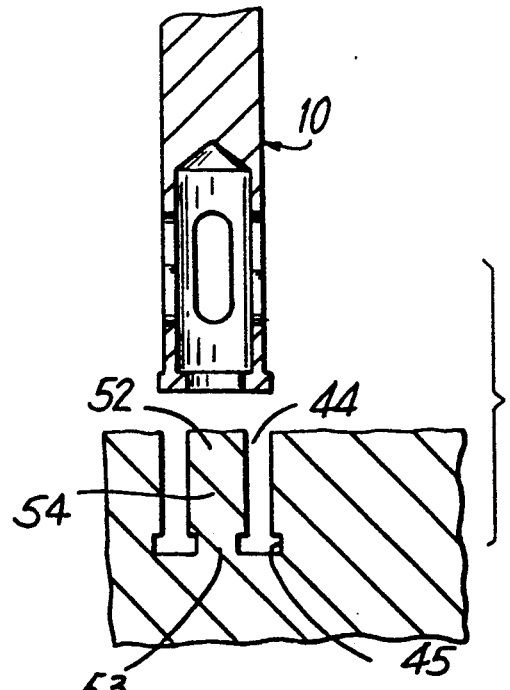
Figure 47:
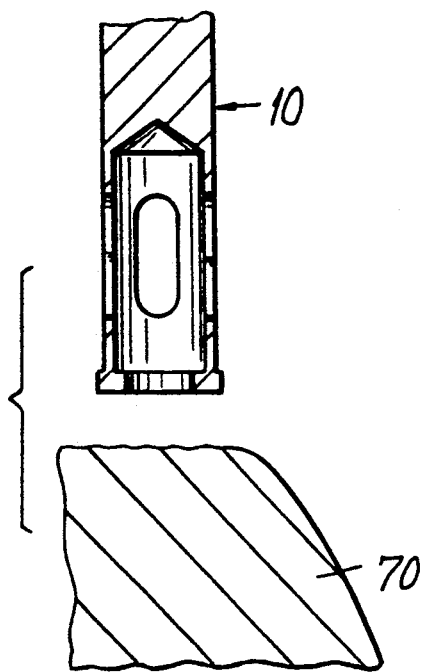
FIG. 47 through FIG. 54 are schematic cross sectional representations, in chronological order, depicting of the use of the tool of FIG. 1 to excavate a hole in a jaw bone in a manner to allow the permanent implanting of an insert on which an artificial tooth or dental prosthesis is mounted.
Figure 48:
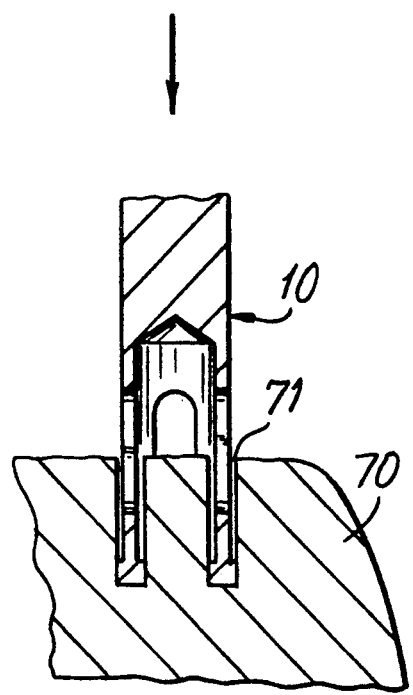
Figure 49:
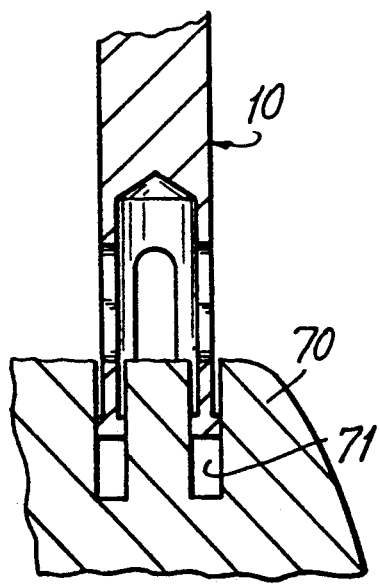
Figure 50:
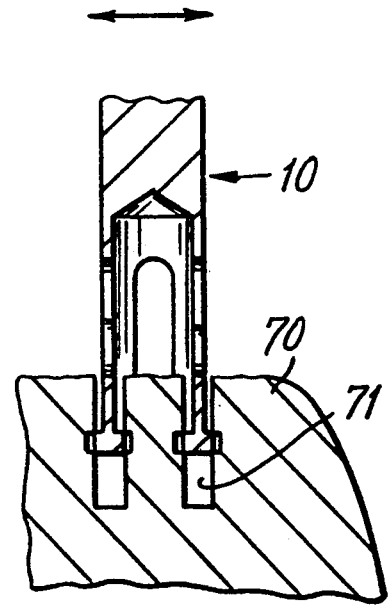
Figure 51:
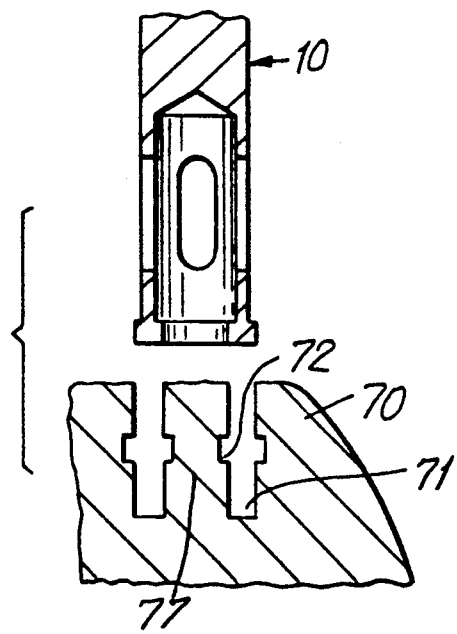
Figure 52:
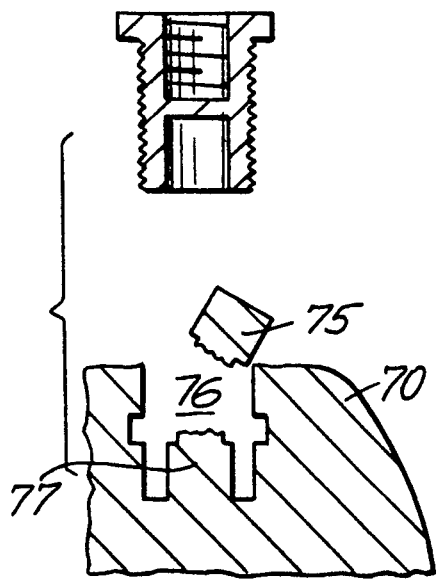
Figure 53:
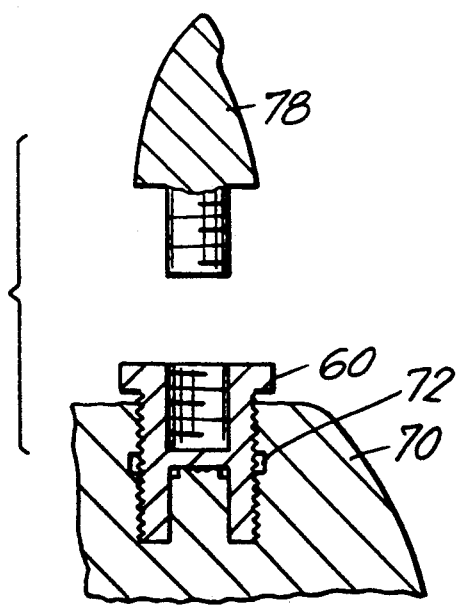
Figure 54:
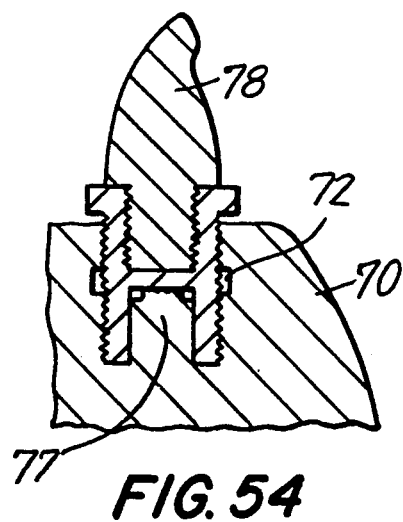
Figure 55:
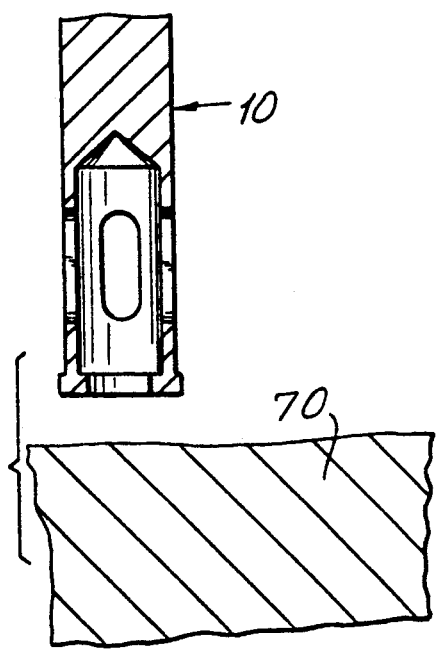
FIG. 55 through FIG. 62 are diagrammatic cross sectional representations, in chronological order, of the use of the tool of FIG. 1 to obtain a core of jaw bone material, crushing the same and use the crushed bone in the augmentation of bone around a tooth.
Figure 56:
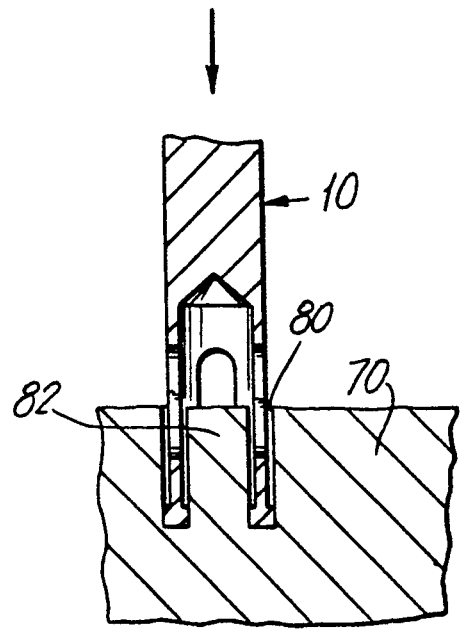
Figure 57:
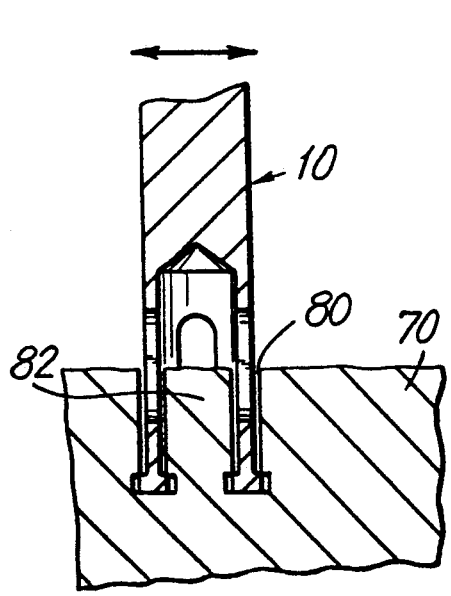
Figure 58:
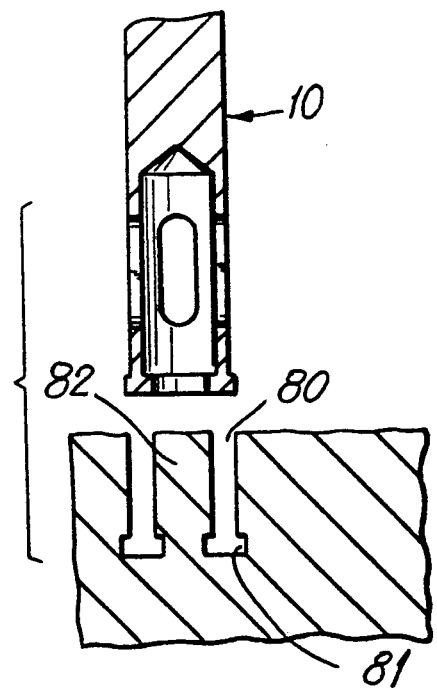
Figure 59:
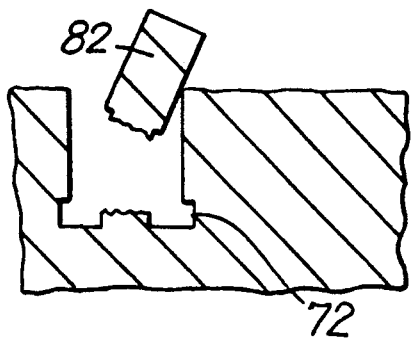

FIGS. 36 through 42 show the use of tool 10 to make a cylindrical opening 44 in tooth 40 for insertion of said insert 45 and the method for such insertion into the cavity 44. As discussed in connection with the making of an annular cavity, tool 10 is moved axially into the tooth body 40, creating an annular hole 44. As shown in FIG. 38, the tool 10 is then moved radially to make an enlarged annular chamber 45 at the bottom of hole 44 and then removed. As a result, there is left a core 52 in the tooth having a narrow portion 53 and an extended portion 54. As shown in FIG. 40, this core may be broken off at the narrow portion 53 and removed, leaving a cavity 55 formed from the hole 44, enlarged portion 45, and a space previously occupied by the extended core portion 54. The insert 45 is then forced into resulting hole 55. The diameter of the central portion 48 of insert 45 is the same, or slightly less than the diameter of the upper portion of hole 55. Accordingly, flange 51 would not normally fit in hole 55. Because of the slot 49, however, the insert 45 will be internally deflected sufficiently to allow the insert 45 to be positioned in cylindrical hole 55, and pressed axially until the flange 51, snaps into the portion of hole 55 formed from the enlarged section 45. This would by itself hold the insert 45 rigidly in place. Of course a cement may be used to further lock insert 45 in place.

Tool 10 may also be used to excavate a cavity 71 in a jaw bone 70 for holding an insert 60 upon which a dental prosthesis may be mounted. FIG. 43 through 46 show an insert 60 for mounting such dental prosthesis in a jaw bone 70. The insert 60 is basically cylindrical in configuration, having a wider cylindrical top 61 with a central opening 62 therein and a cylindrical body portion 63. The external surface of at least part of central body portion 63 is threaded. The opening 62 in the top 61 of the insert 60 is the entrance to a threaded cavity which proceeds approximately half way down the insert body 63, formed in a solid upper portion 65 of such insert 60. Below said solid portion 65, the insert 60 has a hollow cavity 66 having slots or openings 67 therein. These slots or openings 67 are to allow regenerated bone to grow into the insert 60, thereby further fixing and holding the insert 60 in place in a jaw bone.

As seen in FIGS. 47 through 54, tool 10 is moved axially against the jaw 70 to drill an annular passage 71 into the jaw. The tool 10 is the removed part way up the shaft to a portion corresponding to where the top 66A of cavity 66 of insert 60 would be positioned when insert 60 was fitted in the jaw 70. The tool 10 is moved radially to form an enlarged annular chamber 72, and then removed from the jaw 70. After tool 10 is removed, there is left an annular hole 71 having an enlarged portion 72 with a corresponding central core of bone material 77 with a reduced portion corresponding to enlarged section 72. The core 77 is then broken at said reduced portion 72A and removed, leaving a combined chamber 76 with the remaining central core of bone 77 therein. The insert 60 is then installed, by screwing it into the hole 71 in jaw 70. Dental prosthesis 78 is then installed in insert 60. Due to the holes 67 in insert 60 the jaw 70 is allowed to regenerate into cavity 66 and further fix the insert 60 in the jaw 70.

Figure 60:
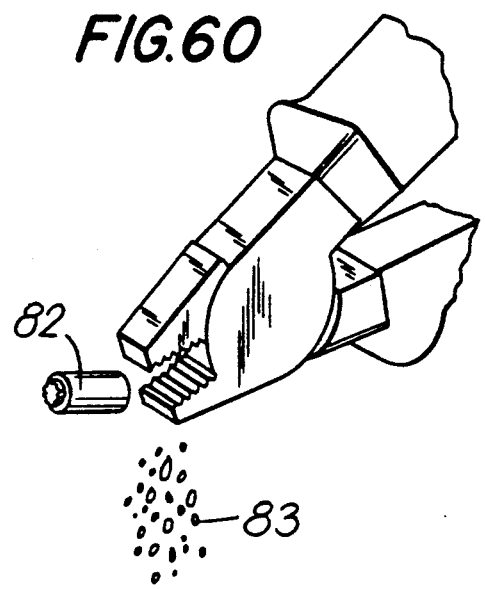
Figure 61:
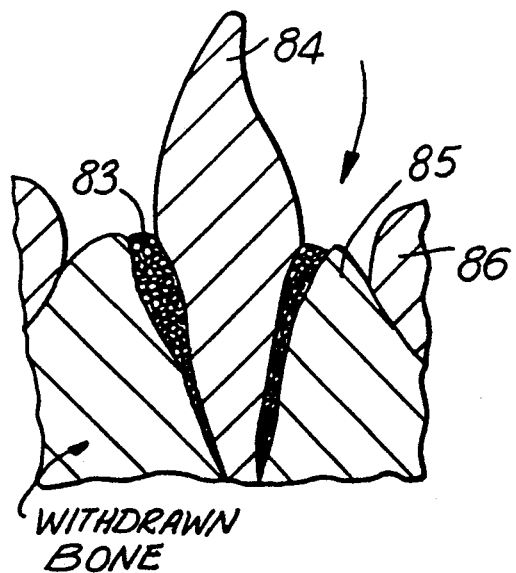
Figure 62:
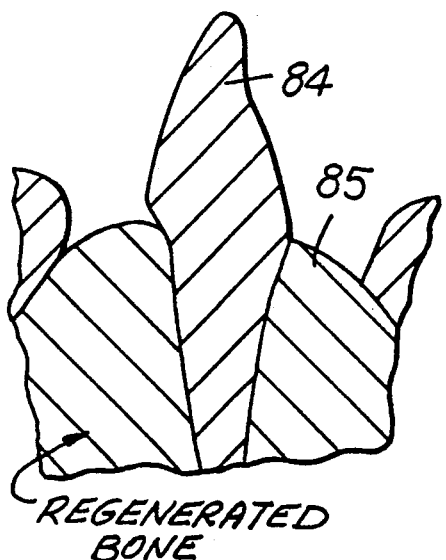

The tool 10 can also be used to obtain material for use to help regenerate bone structure around a tooth. As seen in FIGS. 55 through 59, a core 82 of bone material is obtained by use of tool 10. As done in other application of tool 10, tool 10 is used to make an annular hole 80 in jaw bone 70, which is enlarged at its lower end 81 by radial movement of the tool 10. A core 82 of bone tissue can thus be removed as in other applications of the tool 10. As seen in FIG. 60, the bone tissue is then be crushed to form relatively course bone particles 83. These particles 83 are then positioned around the bone of a tooth 84 between the tooth 84 and the surrounding withered bone 85 below the gum 86. This will aid regeneration of the withered bone 85 around the tooth.

The embodiment of the present invention herein described and disclosed in presented merely as an example of the invention. Other embodiments coming within the scope of the present invention will be readily suggest themselves to those skilled in the art, and shall be deemed to come within the scope of the appended claims.

I claim:

1. A method for securing a dental prosthesis to a tooth where a tooth core is prepared by removing a predetermined amount of enamel from the surface of a tooth, leaving a prepared core adapted to receive a dental prosthesis, comprising forming a channel around the prepared core, inserting a gasket into said channel, positioning a dental prosthesis on said prepared core in contact with said gasket.

2. The method for securing a dental prosthesis in accordance with claim 1 wherein the gasket is formed with a cutaway portion; the dental prosthesis is formed with a corresponding extended portion and the extended portion of the dental prosthesis is moved into position against the cutaway portion of the gasket thereby locking and sealing said prosthesis in place.

3. The method of claim 1 wherein the channel is itself further undercut such that the channel has an enlarged inner secondary channel.

4. The method for securing a dental prosthesis in accordance with claim 1 wherein the undercut portion is made by axially rotating a tool, the tool comprising: an elongated shank, a first end of the shank being adapted to be secured to a driving means; an elongated shaft extending from a second end of said shank opposite said first end, said shaft being hollow for at least part of its length; an annular ring, having an outer diameter greater than the outer diameter of the shaft and attached to the end of the shaft farthest from said shank, the annular ring being coaxial with the shaft and the opening in the annular ring forming an entry into the hollow portion of the shaft, the inner diameter of the hollow portion of the shaft being greater than the inner diameter of the annular ring, and the outer circumferential surface of said annular ring forming a cutting surface of the tool; the method further comprising positioning the outer circumferential surface of the annular ring of said tool against a portion of the prepared tooth core where the channel is desired, applying pressure to the tool radial to its axis, and thereby against the surface of the prepared tooth core, and moving the tool around the outer circumference of the prepared tooth core.

5. The method for securing a dental prosthesis in accordance with claim 4 wherein said channel is further undercut to form an enlarged secondary channel by positioning the annular ring of the tool at right angle to its initial position in forming the channel such that the outer circumferential surface of the annular ring is positioned against a different wall of the channel than the one it abutted during formation of the channel and the bottom of the annular member is positioned against the innermost wall of the channel; applying pressure to the tool radial to its axis such that the outer circumferential surface of the member excavates a secondary channel into the wall of the channel its abuts and moving the tool circumferentially around the tooth in the channel.

6. The method for securing a dental prosthesis in accordance with claim 4 wherein the bottom surface of the annular ring has an abrasive coating thereon; and where said abrasive surface is positioned against said tooth; pressure is applied to the tool along its axis and the bottom of the annular ring thereby further shapes the shoulder of the tooth core to receive the dental prosthesis, simultaneously with the outer circumferential surface of said annular ring being used to form said channel.

7. A method of using the tool of claim 4 for forming an undercut channel in a tooth comprising moving the tool in the desired pattern of the undercut, so that the outer circumferential surface of the annular ring excavates the desired channel.

8. The method for securing a dental prosthesis in accordance with claim 1 wherein simultaneously with the formation of said groove, the shoulder of the prepared tooth core is further shaped to receive a dental prosthesis.

9. A method in accordance with claim 1 wherein the gasket fills the groove.

10. An insert to be mounted in a tooth to support a dental prosthesis comprising a hollow cylindrical body portion with enlarged flanges at either end, the first flange being adapted to support a dental prosthesis, the second flange having a slot extending through it and said surrounding body of the insert to allow flexure of the portion of the insert near the second flange, the first and second flange having centrally located openings in communication with said hollow portion.

11. The insert according to claim 10 wherein the first flange is knurled to better act as a post to hold a dental prosthesis.

12. An insert in accordance with claim 10 wherein there is a small cylindrical opening in the central portion of the second flange which extends part way into the body of the insert.

13. A method for securing an insert in a tooth, the insert comprising a hollow cylindrical body portion with enlarged flanges at either end, the first flange being adapted to support a dental prosthesis, the second flange having a slot extending through it and said surrounding body of the insert to allow flexure of the portion of the insert near the insert to allow flexure of the portion of the insert near the second flange, and the first and second flange having centrally located openings in communication with said hollow body portions; the method comprising cutting an annular hole into the surface of the tooth of a size that the outer diameter of the annular hole is approximately the same as the outer diameter of the body portion of the insert, leaving a central core of tooth material; expanding the size of the bottom of the annular hole both radially inwardly and outwardly of said hole to form an enlarged portion of the hole, without changing the shape of the remainder of the annular hole, placing a bonding agent in said annular hole and enlarged portion; forcing the end of said insert having the second flange into said hole until the second flange fits into said enlarged portion of said hole, thereby locking said insert in place.

14. The method in accordance with claim 13 wherein any excess bonding agent is forced through an opening in the first flange of said insert and then removed.

15. The method in accordance with claim 13 wherein the sides of the insert near the second flange are forced together during insertion.

16. The method in accordance with claim 13 wherein prior to positioning of the insert, the central core of tooth material in the annular hole is removed.

17. The method in accordance with claim 13 where a tool is used to form the annular hole by axially rotating said tool; the tool comprises an elongated shank, a first end of the shank being adapted to be secured to a driving means; an elongated shaft extending from the second end of said shank opposite said first end, said shaft being hollow for at least part of its length; an annular ring, having an outer diameter greater than the outer diameter of the shaft and attached to the end of the shaft farthest from said shank, the annular ring being coaxial with the shaft and the opening in the annular ring forming an entry into the hollow portion of the shaft, the inner diameter of the hollow portion of the shaft being greater than the inner diameter of the annular ring, and the outer circumferential surface of said annular ring forming a cutting surface of the tool; and an abrasive coating secured to the inner circumferential surface and the bottom of the annular ring; the method further comprising positioning said tool so that the bottom of the annular ring is against the tooth at the point in which the annular hole is desired; applying pressure to the tool along its axis thereby forcing it into the tooth; continuing said axial movement until an annular hole of the desired depth is formed, leaving a core of tooth material, moving the tool circumferentially around the core of tooth material in the annular hole while applying pressure to the tool radial to its axis, thereby forming said enlarged annular space which undercuts said core of tooth material.

18. A method of forming an annular opening in a tooth or bone with an enlarged portion comprising axially rotating a tool, the tool comprising an elongated shank, a first end of the shank being adapted to be secured to a driving means; an elongated shaft extending from the second end of said shank opposite said first end, said shaft being hollow for at least part of its length; an annular ring, having an inner diameter greater than the outer diameter of the shaft and attached to the end of the shaft farthest from said shank, the annular ring being coaxial with the shaft and the opening in the annular ring forming an entry into the hollow portion of the shaft, the inner diameter of the hollow portion of the shaft being greater than the inner diameter of the annular ring, and the outer circumferential surface of said annular ring forming a cutting surface of the tool; and an abrasive coating secured to the inner circumferential surface and the bottom of the annular ring; positioning said tool so that the bottom of the annular ring is against the tooth or bone at the point in which the annular hole is desired; applying pressure to the tool along its axis thereby forcing it into the tooth or bone; continuing said axial movement until an annular hole of the correct depth is formed, leaving a core of tooth or bone material; moving the tool circumferentially around said core of material in the annular hole while applying pressure to the tool radial to its axis, thereby forming a both inwardly and outwardly enlarged annular space which undercuts said core of tooth material.

19. The method of forming an annular opening in accordance with claim 18, wherein after forming the annular hole but before applying radial pressure to the tool, the tool is partially drawn up the annular hole so that when the tool has pressure applied radial to its axis, it will undercut the tooth core at a point between either end of the annular hole.

20. A method for anchoring a dental prosthesis in the jaw comprising cutting an annular cavity into a jawbone, leaving a central core of bone in the annular opening; undercutting the core at an intermediate axial location in said cavity by forming a channel therein; breaking off the core at said channel; positioning an insert comprising: a cylindrical body portion having a wider cylindrical top portion at one end, with a central opening therein, the external surface of said cylindrical body portion being partially threaded, the threaded portion extending axially from the first end adjacent the wider tip portion, the tip portion and the externally threaded body portion being hollow and having an internal cylindrical surface, the internal cylindrical surface having mounting means adapted to mate with and support a dental prosthesis, a substantial portion of the remainder of the body portion of the insert being hollow, having an unthreaded cavity therein, with the hollow portion of the insert surrounding the remaining portion of the bone core.

21. A method in accordance with claim 20 wherein the channel is formed in the core at a height corresponding to the height of the unthreaded chamber in the insert.

22. A method in accordance with claim 21 wherein said annular opening is made by axially rotating a tool comprising an elongated shank, a first end of the shank being adapted to be secured to a driving means; an elongated shaft extending from the second end of said shank opposite said first end, said shaft being hollow for at least part of its length; an annular ring, having an outer diameter greater than the outer diameter of the shaft and attached to the end of the shaft farthest from said shank, the annular ring being coaxial with the shaft and the opening in the annular ring forming an entry into the hollow portion of the shaft, the inner diameter of the hollow portion of the shaft being greater than the inner diameter of the annular ring, and the outer circumferential surface of said annular ring forming a cutting surface of the tool and an abrasive coating secured to the inner circumferential surface and the bottom of the annular ring; positioning said tool so that the bottom of the annular ring is in contact with the tooth at the point in which the opening is desired; applying pressure to the tool along its axis thereby forcing the tool into the tooth until the desired depth is reached, partially withdrawing said tool out of said annular cavity, moving said tool circumferentially around said core while applying pressure to the tool radial to its axis, thereby undercutting the core by forming a channel therein.

23. A method for the regeneration of withered bone surrounding a tooth comprising cutting an annular hole into a jaw bone leaving a core of bone material; enlarging the bottom of said hole to undercut the central core of material left in the annular opening; breaking off said central core; coarsely crushing said central core; packing said coarsely crushed bone material around said tooth between the tooth and the withered bone below the gums, thereby aiding regeneration of the withered bone around the tooth.

24. A method in accordance with claim 23 wherein the undercut central core is formed by axially rotating a tool comprising an elongated shank, a first end of the shank being adapted to be secured to a driving means; an elongated shaft extending from the second end of said shank opposite said first end, said shaft being hollow for at least part of its length; an annular ring, having an outer diameter greater than the outer diameter of the shaft and attached to the end of the shaft farthest from said shank, the annular ring being coaxial with the shaft and the opening in the annular ring forming an entry into the hollow portion of the shaft, the inner diameter of the hollow portion of the shaft being greater than the inner diameter of the annular ring, and the outer circumferential surface of said annular ring forming a cutting surface of the tool; and an abrasive coating secured to the inner circumferential surface and the bottom of the annular ring; positioning said tool so that the bottom of the annular ring is against the tooth at the point in which the annular hole is desired; applying pressure to the tool along its axis thereby forcing the tool into the tooth; continuing said axial movement until an annular hole of the desired depth is formed leaving a core of tooth material; moving the tool circumferentially around the core of tooth material in the annular hole while applying pressure to the tool radial to its axis, thereby forming an enlarged annular space which undercuts said core of tooth material.

* * * * *